(12) United States Patent
Zambaux et al.

(10) Patent No.: US 8,202,258 B2
(45) Date of Patent: Jun. 19, 2012

(54) PLASTIC NEEDLE AND DEVICES COMPRISING IT

(75) Inventors: Jean-Pascal Zambaux, Allonzier la Caille (FR); Jean Rousseau, Villers Rottin (FR)

(73) Assignee: Seft Holding SA, Sion (CH)

( * ) Notice: Subject to any disclaimer, the term of this patent is extended or adjusted under 35 U.S.C. 154(b) by 1443 days.

(21) Appl. No.: 10/571,314

(22) PCT Filed: Sep. 11, 2003

(86) PCT No.: PCT/EP03/11211
§ 371 (c)(1),
(2), (4) Date: Mar. 9, 2006

(87) PCT Pub. No.: WO2005/023327
PCT Pub. Date: Mar. 17, 2005

(65) Prior Publication Data
US 2007/0073249 A1    Mar. 29, 2007

(51) Int. Cl.
*A61M 5/32*        (2006.01)
(52) U.S. Cl. ........................................ 604/272; 604/414
(58) Field of Classification Search .......... 604/158–173, 604/263–279, 284, 523–539, 411–416
See application file for complete search history.

(56) References Cited

U.S. PATENT DOCUMENTS

| | | | | |
|---|---|---|---|---|
| 3,608,550 | A * | 9/1971 | Stawski | 604/414 |
| 5,057,092 | A * | 10/1991 | Webster, Jr. | 604/527 |
| 5,637,399 | A * | 6/1997 | Yoshikawa et al. | 428/369 |
| 5,872,159 | A | 2/1999 | Cougoulic | |
| 6,348,055 | B1 * | 2/2002 | Preissman | 606/94 |
| 2002/0055721 | A1 * | 5/2002 | Palasis et al. | 604/265 |
| 2002/0102185 | A1 | 8/2002 | Tatsumi | |
| 2003/0032929 | A1 | 2/2003 | McGuckin | |
| 2003/0195327 | A1 | 10/2003 | King | |

FOREIGN PATENT DOCUMENTS

| | | |
|---|---|---|
| DE | 100 43 787 | 1/2002 |
| GB | 809146 | 2/1959 |
| JP | 55-25081 U | 2/1980 |
| JP | 5-70548 U | 9/1993 |
| JP | 2003 250821 | 9/2003 |
| WO | 02/00271 | 1/2002 |
| WO | 02/087650 A1 | 11/2002 |

* cited by examiner

*Primary Examiner* — Kevin C Sirmons
*Assistant Examiner* — Phillip Gray
(74) *Attorney, Agent, or Firm* — Dennison, Schultz & MacDonald

(57) ABSTRACT

The invention relates to a plastic needle.
The plastic needle of the invention is made of a polyaryletherecetone polymer.
The invention finds industrial applicability in particular in medical and analysis fields.

19 Claims, 2 Drawing Sheets

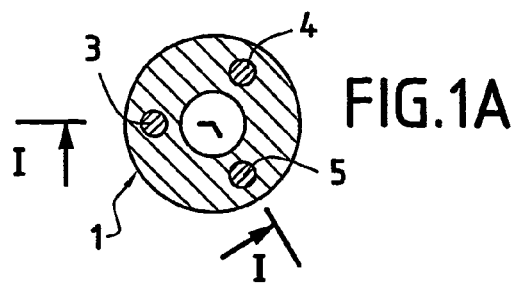
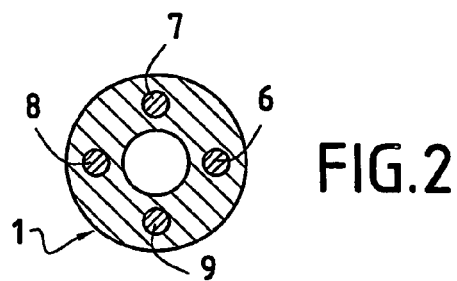
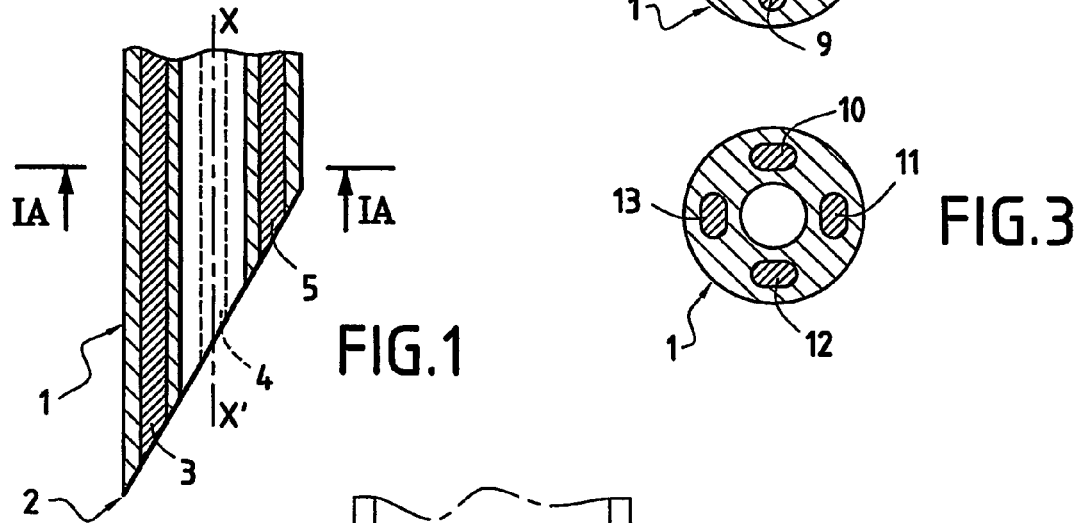
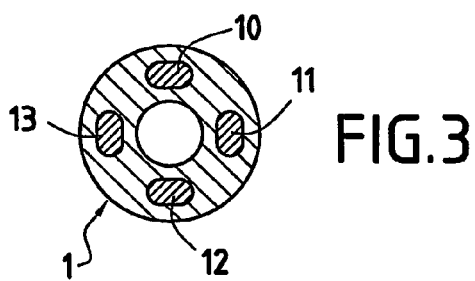
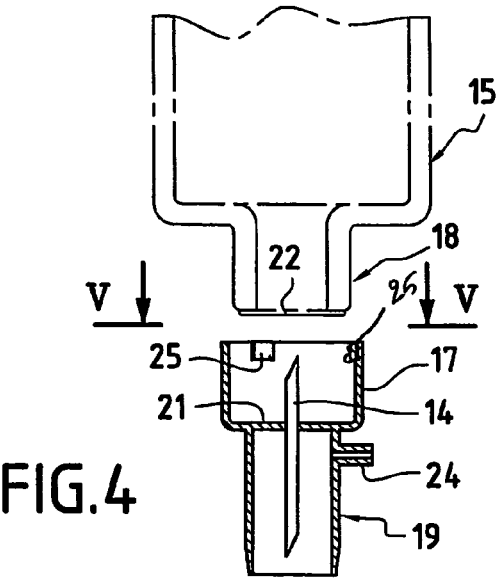
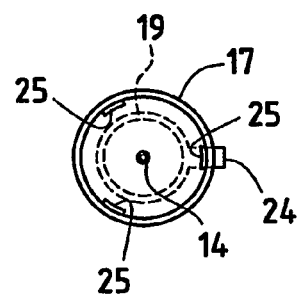
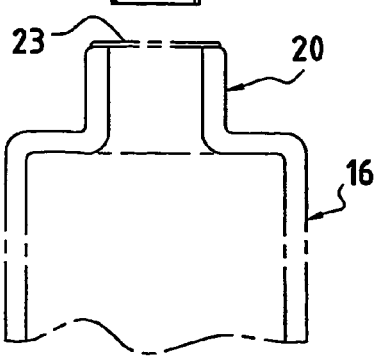

PLASTIC NEEDLE AND DEVICES COMPRISING IT

This application is a filing under 35 USC 371 of PCT/EP2003/011211, filed Sep. 11, 2003.

BACKGROUND OF THE INVENTION

The invention relates to a plastic needle. It also relates to a syringe and a recipient connector comprising said plastic needle.

Pyrogens or pyrogenic substances are impurities which, where present in a pharmaceutical product intended for being administered to a patient, cause a fever reaction when the pharmaceutical product is actually administered.

In the medical field, numerous devices comprise needles for injection and/or perforation which enable the flow of a pharmaceutical product, generally a liquid.

Such needles intended for containing and transporting a pharmaceutical product must not only be sterile and sterilizable, but also apyrogenic, i.e. they contain no pyrogens, and must be depyrogenisable, i.e. they must be capable of undergoing a process which removes any pyrogens which they may contain.

In fact, in order to depyrogenise such needles, they have to be heated up to 253° C. for one hour.

This is one of the reasons why needles for injection of a pharmaceutical product into human tissue are generally made of metal. Another reason is that these needles for injection into human tissue have to be very fine in order to limit the pain experienced by the patient, whilst retaining adequate strength and rigidity for penetration of the skin and the subcutaneous layers.

However, metal needles, once they have been used, cannot be easily disposed of, and this gives rise to a sanitary health problem because of contamination accidents arising from contact with (or accidental re-utilization of) these non-sterilized and non-depyrogenised needles In order to solve this problem of needles for injection of pharmaceutical products, particularly into the human body, needles made of plastic have been proposed.

In particular, international patent application WO 00/72901 describes a process for the manufacture of such a plastic injection needle in which the employed plastic is a liquid crystalline polymer comprising 73% hydroxy benzoic acid and 27% hydroxy naphthoic acid.

However, plastic needles of the prior art cannot be heated up to 253° C. for one hour without becoming deformed.

In reality, where a plastic needle for use in the medical field is employed, it is for single use only and it cannot be depyrogenised, but is manufactured under conditions such that it is free of pyrogens. However, once it has been taken out from its pack and utilized, it is not depyrogenisable.

Furthermore, since these needles are not depyrogenisable, it is not possible, not even before first utilization, to depyrogenise them in order to be certain that they are indeed free of pyrogens. Indeed, production problems or problems occurring during their transport or handling may have caused contamination with pyrogens.

Needles are also employed as a means for perforation and flow of a product contained in a recipient to a different recipient, interconnected by a recipient or bottle connector.

A bottle connector of this type is generally made up of a first hollow section intended for fitting around the neck of a first recipient and a second hollow section intended for fitting into the neck of a second recipient, such hollow sections being separated from each other by a horizontal wall at the center of which there is a means of perforation, elastic capsules of the recipients to be connected together, and a passage for flow of products, generally liquid, contained in one bottle towards the other bottle.

This means of perforation and of inducing flow may be a needle similar to an injection needle but with larger internal and external sections.

Again, with regard to bottles containing pharmaceutical products, for example for transfusion to a human being, it is important to assure the sterility and absence of pyrogens at least in the materials making up the needle which is used for perforation and flow.

Accordingly, in these needles of connectors of the prior art, we encounter the same problems as in respect of the above described injection needles.

SUMMARY OF THE INVENTION

The purpose of the invention is to solve these problems by proposing a needle, in particular for fitting to an injection syringe or for fitting to a bottle connector, which is both depyrogenisable and easy to dispose of.

For this purpose, the invention proposes a needle made up of a cylindrical body which is extended along a longitudinal axis X-X' at least one end of which is beveled, characterized in that it is made of a polyarylethercetone polymer of the following formula (1):

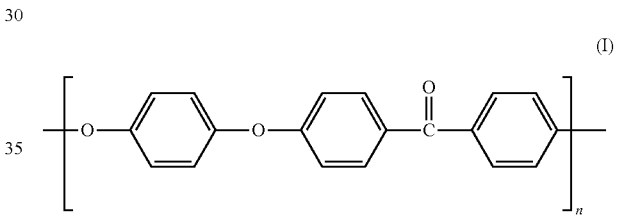

The formula (1) polyarylethercetone polymer may also comprise fillers selected from carbon fibers, glass fibers, graphite granules, polytetrafluoroethylene (PTFE) granules, black carbon granules and mixtures of two or more of the above.

In one preferred mode of production, it also comprises at least three reinforcements wires embedded in the polyarylethercetone polymer of formula (1), extending parallel to the longitudinal axis X-X' over the whole of the length of the hollow body, being even-tensioned and equidistant from each other and distributed such that each pair of wires defines an identical center angle.

Preferably, the said at least three wires are made of 316 stainless steel.

The said at least three wires may be of circular cross-section.

They may also be of elliptical cross-section.

The hollow body preferably has a circular section.

In one particular mode of manufacture, the hollow body is beveled at both ends.

Another object of the invention is an injection syringe made up of a piston, a pump body equipped with an end-fitting for fitting of an injection needle, characterized in that it is equipped with a needle according to the invention.

In a preferred embodiment, the pump body fitted with its end-fitting and the piston of the syringe according to the invention are also made of the polyarylethercetone polymer of formula (1), comprising, or not, fillers selected from glass fibers, carbon fibers, graphite granules, polytetrafluoroethylene (PTFE) granules, carbon black granules and mixtures of two or more of the above.

Yet another object of the invention is a connector for recipients made up of a first hollow section suitable for fitting around the neck of a first recipient, a second hollow section suitable for fitting into the neck of a second recipient, with the first hollow section and the second hollow section being separated from each other by a horizontal wall, and a means for perforation of the elastic capsules of the recipients, characterized in that the means of perforation is a needle according to the invention, located at the center of the horizontal wall.

Preferably, the second hollow section of the connector of the invention also comprises a port for the admission of gas.

Preferably, too, the first hollow section of the connector according to the invention also comprises means for fitting the connector to the neck of the recipient.

In a preferred embodiment of the connector of the invention, the first hollow section, the second hollow section and the separating wall are made up of a polyarylethercetone polymer of formula (1) which may also comprise fillers selected from the carbon fibers, glass fibers, graphite granules, polytetrafluoroethylene (PTFE) granules and carbon black granules and mixtures of two or more of the above.

BRIEF DESCRIPTION OF THE DRAWINGS

The invention will be best be understood, and the other purposes, advantages and features of it best understood, by reading the explanatory description which follows and which is provided with references to figures, where:

FIG. 1 is a partial longitudinal section view along axis X-X' of the end of a needle according to a first embodiment of the invention, FIG. 1a is a transverse section view along axis IA-IA of the needle according to this first embodiment of the invention, FIG. 2 is a transverse section view of a needle according to a second embodiment of the invention, FIG. 3 is a transverse section view of a needle according to a third embodiment of the invention, FIG. 4 is a longitudinal section view of the connector according to an embodiment of the invention before fitting to the bottle to which it is intended to be connected, FIG. 5 is a transverse section view of the connector according to the invention represented in FIG. 4.

DESCRIPTION OF THE PREFERRED EMBODIMENTS

Figure 6:
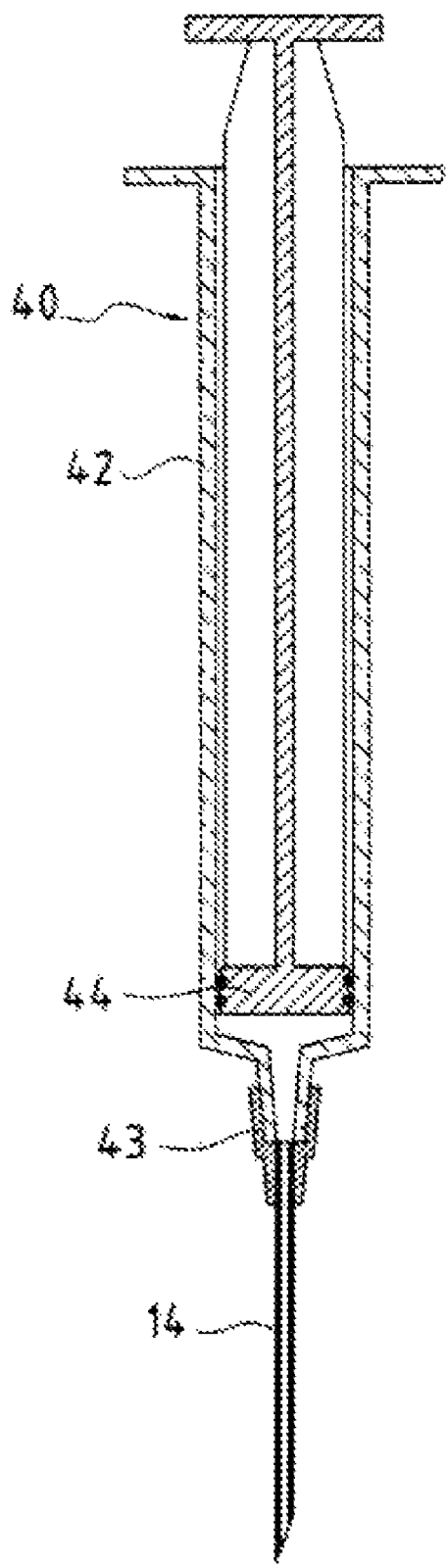
FIG. 6 is a partial longitudinal cross-section view along axis X-X' of FIG. 1.

Firstly, we shall describe the needle according to the invention by reference to FIGS. 1 and 1a. As we can see from FIGS. 1 and 1a, the needle according to the invention is made up of a hollow cylindrical body referred 1 and which longitudinally extends along axis X-X'. This hollow body provides a duct for flow of preferably a liquid particularly a pharmaceutical liquid to be injected or transfusioned.

This needle has at least one beveled end, referenced 2 in FIG. 1, enabling perforation, in particular of human tissue and recipient capsules containing pharmaceutical products.

The essential feature of the invention is that this hollow, cylindrical body, which has at least one beveled end, is made of a polyarylethercetone polymer of the following formula (1):

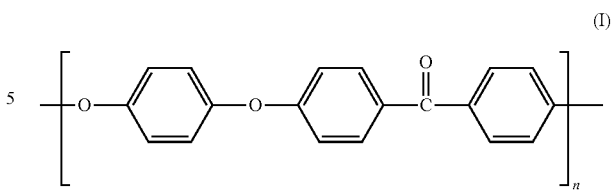

This polymer is a oxy-1,4-phenylene-oxy-1,4 phenylene carbonyl-1,4 phenylene, particularly sold under the trademark PEEK®, by the Company VICTREX®.

This polymer is a semi-crystalline aromatic linear polymer whose melt temperature is 343° C. and whose glass transition temperature is 143° C.

This material is entirely biocompatible with human tissues, and is intrinsically pure, with very low levels of release of extractable gas and ions.

The operating temperature of this polymer is approximately 260° C. with a softening temperature which may reach 315° C.

Accordingly, needles of the invention which are made of this material are perfectly depyrogenisable, i.e. they can be heated to 253° C. for one hour without suffering any deformation or damage to their chemical and mechanical properties.

In a second embodiment of the needle of the invention, and in order to improve these temperature-resistance and rigidity properties, the needle of the invention is made from a polyarylethercetone polymer of formula (1) comprising fillers selected from: glass fibers, carbon fibers, graphite granules, polytetrafluoroethylene granules and carbon black granules.

However, particularly for injection of a pharmaceutical product into human tissues, the injection needle must be very fine in order to minimize pain and tissue damage for the patient.

In fact, needles for injection into human tissues should preferably have an external diameter of approximately 0.7 mm and an internal diameter of approximately 0.25 mm, which consequently means that the thickness of the wall of the needle is approximately 0.25 mm. At such wall thicknesses, rigidity; i.e. the resistance to deformation, of the needle of the invention made up solely of the polyarylethercetone polymer of formula (1), whether or not it comprises charges, may be too low.

Consequently, in a particularly preferred embodiment, the needle of the invention also comprises at least three reinforcement wires which are noted 3, 4 and 5 in FIGS. 1 and 1a. These at least three wires extend parallel to the longitudinal axis X-X' of hollow body 1 and from one end to the other of hollow body 1. These at least three reinforcement wires are even-tensioned throughout their length and are located equidistant one from another, with each pair of wires 3,4; 4,5 and 3,5 defining an identical center angle.

Preferably, these at least three wires embedded in the walls made of polyarylethercetone polymer of the formula (1) are made of 316 stainless steel.

Of course, and as illustrated in FIGS. 2 and 3, a larger number of reinforcement wires, for example four reinforcement wires referred 6, 7, 8 and 9 in FIGS. 2 and 10, 11, 12 and 13 in FIG. 3 may be present provided that, as described above, they are even-tensioned throughout their length, are parallel to longitudinal axis X-X' of body 1 and are equidistant one from another, with each pair of wires defining an identical center angle.

In the same way, these reinforcement wires may be of a circular section as represented in FIG. 1a and in FIG. 2 or may be elliptical as represented in FIG. 3.

If they are of circular section, their preferred diameter is approximately 0.1 mm.

If they are of elliptical section, their main axis is approximately 0.15 mm.

At such wire sizes, when the needle of the invention is exposed to flame or high-temperature heating, in order to render it unusable and to prevent the possibility of puncturing from its beveled end, the wires will also melt and the sanitary safety of the needles of the invention will be maintained.

Hollow cylindrical body 1, being a needle for injection into human tissues, preferably has a circular cross-section in order to minimize pain upon insertion of the needle into human tissues. Relating, again, to a needle for injection of pharmaceutical products into human tissues, only one end of the needle will be beveled, with the other end fitting with the syringe unit.

Accordingly, a further object of the invention is a syringe 40 for injection of pharmaceutical products, particularly into human tissues, made up of a pump body 42 which also acts as a reservoir for the pharmaceutical product to be injected, equipped with an end-fitting 43 onto which an injection needle 14 is fitted, and a piston 44 for propelling the pharmaceutical product through the needle 14, as this syringe comprises an injection needle 14 of the invention.

In a more particularly preferred embodiment, the syringe will be made entirely of a polyarylethercetone polymer of formula (1), which means that the piston, the pump body equipped with its end fitting and the needle itself will entirely be made of such a polymer.

Of course, and in another embodiment of the syringe of the invention, the pump body equipped with its end-fitting and the piston may, in the same way as the needle of the invention, be made of a polyarylethercetone polymer of formula (1) charged with fillers selected from glass fibers, carbon fibers, graphite granules, polytetrafluoroethylene (PTFE) granules and carbon black granules, and mixtures of two or more of the above and, if necessary, reinforced by at least three reinforcement wires.

Although we described the needle of the invention, above, as having a single beveled end and a circular cross-section, the needle of the invention may also, as represented in FIGS. 4 and 5, where it is referenced 14, have both ends beveled.

Likewise, hollow cylindrical body 14 may be of a square, rectangular or trapezoidal section, as desired.

In this case, in fact, the needle of the invention will not be used for injecting a pharmaceutical product directly into human tissues but, for example and as represented in FIGS. 4 and 5, will provide the means of flow for a pharmaceutical product, preferably a liquid, comprised in a first recipient noted 15 in FIGS. 4 and 5 to a second recipient, noted 16 in FIGS. 4 and 5 and a means for perforation of the elastic capsules, noted 22 and 23 in FIGS. 4 and 5, of these recipients.

In this instance it relates to a needle for connection of recipients or bottles.

For example, it will be possible for recipient 15 to contain a pharmaceutical liquid to be transferred to a transfusion pouch 16 which itself will be connected to the body of a patient.

Accordingly, a third object of the invention is a needle which provides the means for perforation and flow of the product for a bottle connector.

The connector itself is a fourth object of the invention.

This connector will now be described by reference to FIGS. 4 and 5.

A bottle connector, particularly for bottles containing pharmaceutical products, is essentially made up of:
  of an initial hollow section, noted 17 in FIGS. 4 and 5, and suitable for fitting around the neck, noted 18, of a first recipient noted 15,
  a second hollow section, noted 19 which is suitable for fitting into the neck, noted 20 of a second recipient, noted 16, with the first hollow section 17 and the second hollow section 19 being separated from each other by a horizontal wall, noted 21, in the center of which there is a means of perforation, noted 14, for elastic capsules, noted 22 and 23, of recipients 15 and 16.

Means of perforation 14 also provides a duct for flow of the contents of bottle 15 to bottle 16.

In order to enable passage of the contents of bottle 15 to bottle 16, it is preferable that the connector also comprises, preferably on second hollow section 19, a port noted 24 enabling the admission of a gas, preferably an inert gas.

Likewise, in order to enable secure and well-aligned fitting of the connector around neck 18 of first recipient 15 and in neck 20 of second recipient 16, the connector of the invention preferably further comprises a means for hooking of the first hollow section 17 of the connector around neck 18 of recipient 15. Such means may, for example, as represented in FIGS. 4 and 5 be clipping means noted 25.

The essential feature of the connector of the invention is that it comprises a needle of the invention made of a polyarylethercetone polymer of formula (1), charged or not charged, comprising, or not, at least three reinforcement wires.

However, in a similarly preferred mode of production, the connector of the invention is made entirely of a polyarylethercetone polymer of formula (1), charged or not with the above-described fillers and also comprising or not reinforcement wires.

Upon entire fitting of the connector of the invention around and within the neck of recipients 15 and 16, respectively, which it is intended to connect, needle 14 perforates elastic capsules 22 and 23 and enables passage of the product contained in recipient 15 into recipient 16.

The needle, the syringe and the connector of the invention may be made by any process known to a specialist, such as a process of injection molding, an extrusion process or an extrusion under tension process called the pultrusion process whereby the reinforcement wires are held under tension during their passage, and that of the polymer matrix, in the extrusion die.

Of course, the invention is by no means limited to the embodiments described and illustrated above and given as non-exhaustive examples, only.

Accordingly, although the needle and the connector of the invention have been described for utilization with pharmaceutical liquids, the needle according to the invention is also employed in other fields, such as, for example, as a needle for sampling and injecting chemical products for analysis, or as a needle for injecting and sampling for chromatographic analysis apparatus.

The invention claimed is:

1. Needle comprising a cylindrical hollow body with a central lumen therethrough surrounded by a wall, the body being beveled at least one end thereof, and extending along a longitudinal axis X-X', the wall in contact with the central lumen comprising a polyaryletherketone polymer of formula (1):

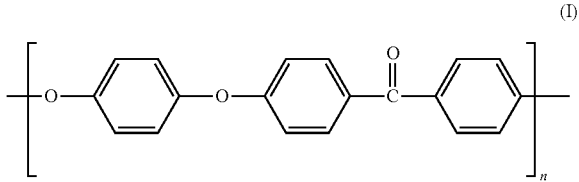

the needle further comprising a metal reinforcement material consisting essentially of three or four reinforcement stainless steel wires embedded in the polymer and extending parallel to the longitudinal axis X-X', and being even-tensioned throughout the length of the hollow body, and distributed such that any pair of said wires defines an identical center angle.

2. Needle according to claim 1, wherein the polymer additionally comprises a filler selected from the group consisting of carbon fibers, glass fibers, graphite granules, polytetrafluoroethylene (PTFE) granules, black carbon granules and mixtures thereof.

3. Needle according to claim 1, wherein the reinforcement wires are made of 316 stainless steel.

4. Needle according to claim 1, wherein the reinforcement wires are of circular section.

5. Needle according to claim 1, wherein the reinforcement wires are of elliptical section.

6. Needle according to claim 1, wherein the hollow body is of circular section.

7. Needle according to claim 1, wherein the hollow body is beveled at both ends thereof.

8. Injection syringe comprising a needle according to claim 1.

9. Syringe according to claim 8, wherein the syringe comprises a polyaryletherketone polymer of formula (1).

10. Syringe according to claim 8, wherein the syringe comprises a polyaryletherketone polymer of formula (1), and a filler selected from the group consisting of glass fibers, carbon fibers, graphite granules, polytetrafluoroethylene (PTFE) granules, carbon black granules and mixtures thereof.

11. Recipient connector comprising:
a first hollow section suitable for fitting around a neck of a first recipient,
a second hollow section suitable for fitting around a neck of a second recipient,
the first hollow section and the second hollow section being separated from each other by a horizontal wall, and
a means of perforation of elastic capsules of the first and second recipients,
wherein the means of perforation is a needle according to claim 7 located at a center of the horizontal wall.

12. Connector according to claim 11, wherein the second hollow section further comprises a port for admission of a gas.

13. Connector according to claim 11, wherein the first hollow section further comprises means for attachment of the connector to a neck of the first recipient.

14. Connector according to claim 11, wherein the first hollow section, the second hollow section and the separating wall are made of a polyaryletherketone polymer of formula (1).

15. Connector according to claim 14, wherein the polyaryletherketone polymer of formula (1) comprises a filler selected from the group consisting of carbon fibers, glass fibers, graphite granules, polytetrafluoroethylene (PTFE) granules, black carbon granules and mixtures thereof.

16. Syringe according to claim 8, wherein the needle polymer additionally comprises a filler selected from the group consisting of carbon fibers, glass fibers, graphite granules, polytetrafluoroethylene (PTFE) granules, black carbon granules and mixtures thereof.

17. Syringe according to claim 8, wherein the reinforcement wires are made of 316 stainless steel.

18. Connector according to claim 11, wherein the needle polymer additionally comprises a filler selected from the group consisting of carbon fibers, glass fibers, graphite granules, polytetrafluoroethylene (PTFE) granules, black carbon granules and mixtures thereof.

19. Connector according to claim 11, wherein the reinforcement wires are made of 316 stainless steel.

* * * * *